(12) United States Patent
Mayer et al.

(10) Patent No.: US 7,569,128 B2
(45) Date of Patent: Aug. 4, 2009

(54) COULOMETRIC WATER VAPOR SENSOR

(75) Inventors: Daniel W. Mayer, Wyoming, MN (US);
Stephen D. Tuomela, Ramsey, MN (US)

(73) Assignee: Mocon, Inc., Minneapolis, MN (US)

( * ) Notice: Subject to any disclaimer, the term of this patent is extended or adjusted under 35 U.S.C. 154(b) by 853 days.

(21) Appl. No.: 11/012,046

(22) Filed: Dec. 14, 2004

(65) Prior Publication Data

US 2006/0124457 A1    Jun. 15, 2006

(51) Int. Cl.
*G01N 27/26*    (2006.01)
*G01N 27/28*    (2006.01)

(52) U.S. Cl. .................. 204/409; 204/400; 204/430
(58) Field of Classification Search .......... 204/400–435
See application file for complete search history.

(56) References Cited

U.S. PATENT DOCUMENTS

| | | | |
|---|---|---|---|
| 2,830,945 A | 4/1958 | Keidel | |
| 3,081,250 A | 3/1963 | Hall et al. | |
| 3,337,441 A | 8/1967 | Goldsmith | |
| 3,909,386 A * | 9/1975 | Oswin et al. | 204/408 |
| 4,083,765 A | 4/1978 | Lawson | |
| 4,167,457 A * | 9/1979 | Giner | 205/618 |
| 4,267,030 A * | 5/1981 | Breuer et al. | 204/278 |
| 4,276,146 A * | 6/1981 | Coker et al. | 204/266 |
| 4,514,278 A | 4/1985 | Stephens et al. | |
| 4,587,003 A * | 5/1986 | Tantram et al. | 204/412 |
| 4,800,000 A | 1/1989 | Zatko et al. | |
| 4,842,709 A | 6/1989 | Mayeaux | |
| 4,954,238 A | 9/1990 | Kato et al. | |
| 5,164,053 A | 11/1992 | Razaq et al. | |
| 5,199,295 A | 4/1993 | Mettes | |
| 5,322,602 A | 6/1994 | Razaq | |
| 6,024,853 A * | 2/2000 | Kiesele et al. | 204/412 |

FOREIGN PATENT DOCUMENTS

| | | |
|---|---|---|
| EP | 0 326 241 A2 | 2/1989 |
| EP | 0 326 241 A3 | 2/1989 |
| EP | 326421 A | 8/1989 |
| GB | 2 008 772 A | 6/1979 |
| GB | 2008772 A | 6/1979 |

OTHER PUBLICATIONS

F.A. Keidel, (Determination of water by direct amperometric measurement.) (artical), Dec. 1959, vol. 31, No. 12, Wilmington, Delaware.
H.J. Lelie, (Coulometric cell determination of WVT.), Technical Engineering magazine, 1969 issue of Modern Packaging.
Huiliang Huang, (Perfluorosulfonate lonomer-phosphorus pentoxide composite thin films as amperometric sensors for water), issue of Analiytical Chemistry, vol. 63, No. 15 Aug. 1991.

* cited by examiner

*Primary Examiner*—Nam X Nguyen
*Assistant Examiner*—Kourtney R Salzman
(74) *Attorney, Agent, or Firm*—Sherrill Law Offices, PLLC

(57) ABSTRACT

A sensor for detecting water vapor in a gaseous sample. The sensor comprises (a) an anode, (b) a cathode, (c) an electrolyte intermediate the anode and cathode, and (d) an inlet orifice through a central area of the anode or cathode through which the gaseous sample may be placed into contact with the electrolyte. The electrolyte can be retained on a porous electrical-insulating separator located between the interior-facing major surfaces of the anode and the cathode.

21 Claims, 4 Drawing Sheets

COULOMETRIC WATER VAPOR SENSOR

FIELD OF INVENTION

The invention relates to water vapor sensors and more specifically to sensors for measuring trace amounts of water vapor.

BACKGROUND

A wide variety of electrochemical sensors (i.e., sensors employing an electrolytic cell with an anode, cathode and electrolyte) have been developed and employed for detecting and measuring the presence of various chemical compounds, in a sample.

U.S. Pat. Nos. 2,830,945, 4,800,000, 4,842,709 and 5,199,295 each disclose an electrochemical sensor for detecting and measuring water-vapor employing phosphoric acid as the electrolyte. However, the construction and design of these sensors severely limited the accuracy, sensitivity, responsiveness and service life of these sensors.

A strong need exists in certain industry segments for a cost-effective sensor capable of quickly and accurately detecting and measuring the water-vapor content of a sample to concentrations as low as a few parts per billion (ppb). Unfortunately, the currently available sensors, including those described in the patents referenced above, do not meet these requirements.

Accordingly, a strong need continues to exits for a cost-effective sensor capable of quickly and accurately measuring the water-vapor content of a sample to concentrations as low as a few ppb.

SUMMARY OF THE INVENTION

The invention is a sensor for detecting water vapor in a gaseous sample. The sensor comprises (a) an anode, (b) a cathode, (c) an electrolyte intermediate the anode and cathode, and (d) an inlet orifice through a central area of the anode or cathode through which the gaseous sample may be placed into contact with the electrolyte.

In further detail, the sensor includes (a) an anode having an interior-facing major surface and an exterior-facing major surface, (b) a cathode having an interior-facing major surface and an exterior-facing major surface, (c) a gap between the interior-facing major surfaces of the anode and the cathode, (d) an electrolyte within the gap, (e) an inlet orifice through the anode or cathode through which a gaseous sample may flow into a central area of the gap, and (e) an outlet circumscribing the gap through which a gaseous sample introduced into the gap through the inlet orifice may exit the gap.

A preferred embodiment of the sensor includes (a) a cylindrical housing defining a longitudinal lumen having first and second longitudinal ends, (b) a first endcap in longitudinal fixed relationship with the housing over the first longitudinal end of the lumen, (c) a second endcap in longitudinal fixed relationship with the housing over the second longitudinal end of the lumen, and (d) an arrangement retained within the lumen between the endcaps. The arrangement comprises a longitudinally aligned sequence of (i) a first support plate, (ii) a compressed compression spring, (iii) a longitudinally slidable second support plate, (iii) a longitudinally slidable detection assembly comprising a longitudinal sequence of either (A) an anode, a porous electrical-insulating separator, and an electrode with a centrally positioned inlet orifice, or (B) an electrode, a porous electrical-insulating separator, and an anode with a centrally positioned inlet orifice, and (iv) a sealing plate in sealed peripheral engagement with the housing and having a centrally positioned inlet orifice in sealed fluid engagement with the centrally positioned inlet orifice in the anode or cathode.

DETAILED DESCRIPTION OF A PREFERRED EMBODIMENT

Nomenclature
10 Sensor
20 Housing
21 First Longitudinal End of Housing
22 Second Longitudinal End of Housing
29 Lumen Defined by Housing
29x Longitudinal Axis of Lumen
31 First Endcap
31a Longitudinal Outlet Orifice through the Center of the First Endcap
31b Orifice for Electrical Lead through the First Endcap
32 Second Endcap
32a Longitudinal Inlet Orifice through the Center of the Second Endcap
32b Orifice for Electrical Lead through the Second Endcap
40 Detection Assembly
50 Anode
50a Inlet Orifice through the Center of the Anode
51 Interior Major Surface of Anode
52 Exterior Major Surface of Anode
53 Outer Periphery of Anode
60 Cathode
60c Circumferential Passageway
61 Interior Major Surface of Cathode
62 Exterior Major Surface of Cathode
63 Outer Periphery of Cathode
70 Separator
73 Outer Periphery of Separator
79 Gap between the Anode and Cathode defined by the Separator
80 Spring
81 First Support Plate
81a Outlet Orifice through the Center of the First Support Plate
81b Orifice for Electrical Lead through the First Support Plate
81p Post Extending from First Support Plate
82 Second Support Plate
82b Orifice for Electrical Lead through the Second Support Plate
82c Circumferential Passageway
82p Post Extending from Second Support Plate
90 Sealing Plate
90a Longitudinal Inlet Orifice through the Center of the Sealing Plate
90b Orifice for Electrical Lead through the Sealing Plate
91 Inner O-ring 92 Outer O-ring
101 Inlet Tube
102 Exhaust Tube
102p Proximal End of Exhaust Tube
121 Anode Electrical Lead
122 Cathode Electrical Lead
r Radial Direction
x Longitudinal Axis Definitions As utilized herein, including the claims, the phrase "central area" means that area encompassing 50% of the area of a given surface of an object positioned concentrically with the given surface and with a shape which matches the shape of the given surface area. Two examples are given below.

CIRCLE: The Central Area of a circular surface having a diameter of 4 cm is a concentric circle with a diameter as calculated below:

Area of circular surface=$(\pi)(2 \text{ cm})^2$=12.56 cm$^2$

Central Area of circular surface=½ 12.56 cm$^2$=6.28 cm$^2$

Diameter of Central Area circle=(2) (square root of (6.28 cm$^2$/$\pi$))=1.42 cm SQUARE: The Central Area of a square surface having 4 cm sides is a concentric square with side lengths as calculated below:

Area of square surface=(4 cm)$^2$=16 cm$^2$

Central Area of square surface=(½)(16 cm$^2$)=8 cm$^2$

Length of sides of Central Area square=(square root of (8 cm$^2$))=2.83 cm

Description

Construction

Figure 1:
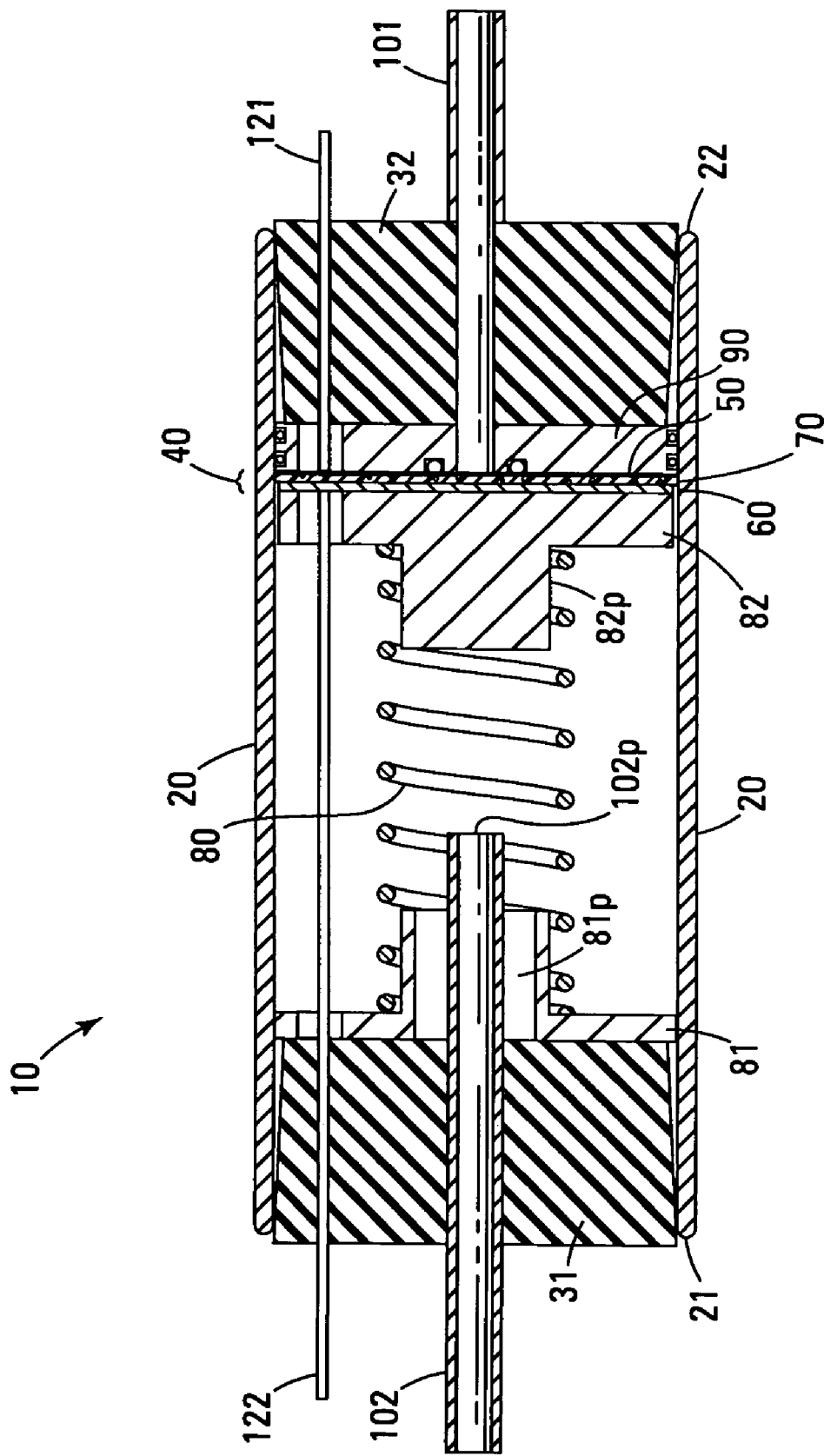
FIG. 1 is a cross-sectional side view of one embodiment of the invention.
Figure 4:
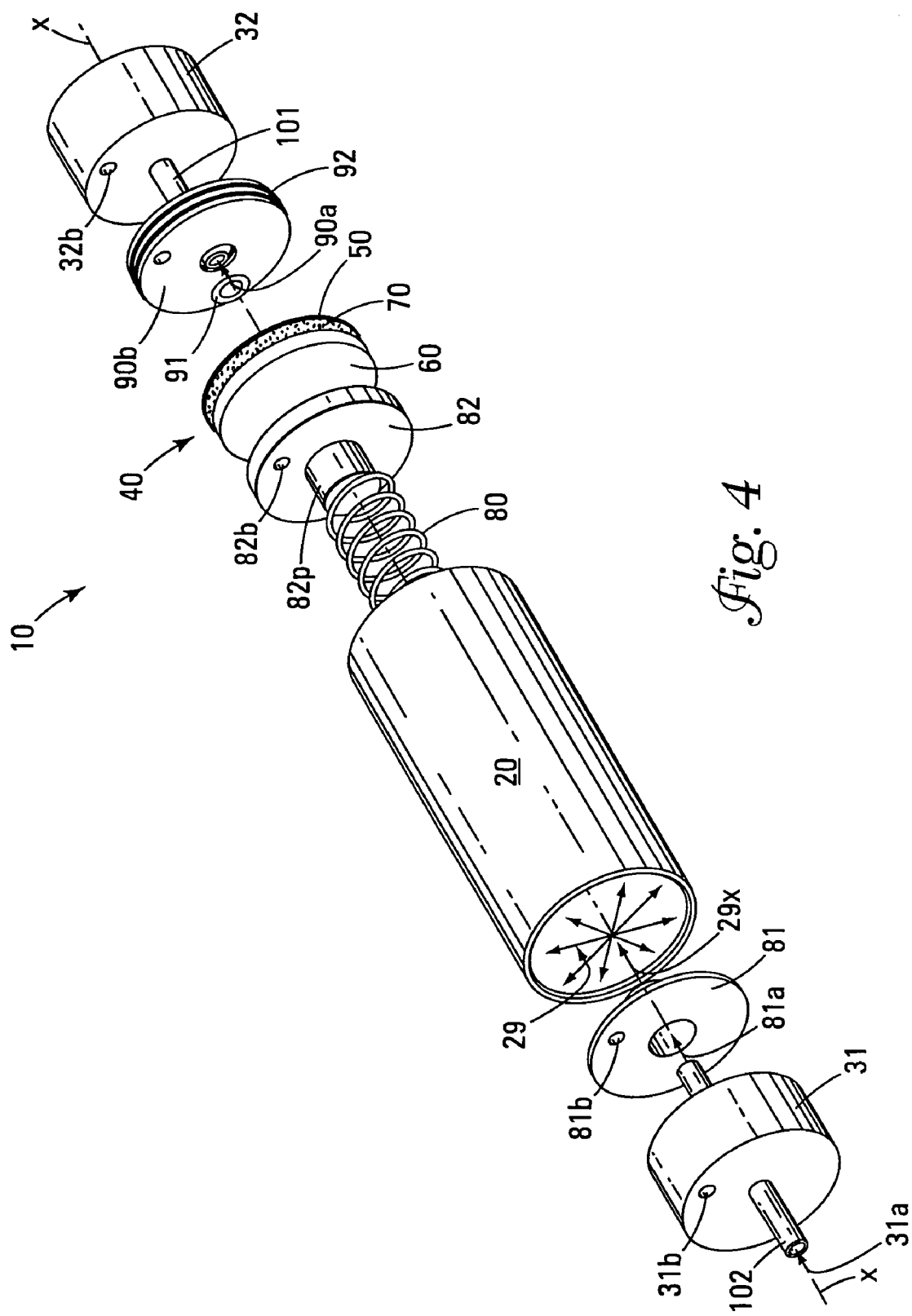
FIG. 4 is a longitudinally exploded perspective view of the invention shown in FIG. 1.

The invention is a sensor 10 for detecting water vapor in a gaseous sample (not shown). As shown in FIGS. 1 and 4, the sensor 10 includes a detection assembly 40 retained in a fixed position within a housing 20 by a retention system (not collectively numbered).

Housing 20

As shown in FIGS. 1 and 4, the housing 20 protectively surrounds the components of the sensor 10—particularly the detection assembly 40—and assists in retaining the components in a fixed, dimensionally stable position relative to one another while permitting controlled flow of a gaseous sample to be tested into contact with the detection assembly 40. The housing 20 may have any desired size and shape effective for achieving these functions, including the hollow cylinder or tube shape as shown in FIGS. 1 and 4.

The housing 20 may be constructed from any material possessing sufficient structural integrity, including specifically, but not exclusively, metals such as aluminum, copper, zinc and steel, plastics such as polyethylene, polypropylene, polyvinyl chloride and polyurethane, glass, wood, etc. Glass is generally preferred due to its highly inert and stable nature.

Detection Assembly 40

As shown in FIGS. 1-4, a detection assembly 40 is retained within the lumen 29 of the housing 20. The detection assembly 40 includes an anode 50, a cathode 60, and an electrolyte (not shown) intermediate the anode 50 and cathode 60. The detection assembly 40 shown in FIGS. 1-4 has the anode 50 positioned upstream from the cathode 60. Alternatively, the cathode 60 may be positioned upstream from the anode 50.

Anode 50

The anode 50 may be constructed from any of the well known materials suitable for use as an anode in an electrolytic cell, provided the material can survive extended exposure to the electrolyte and the high concentration of atomic oxygen evolved at the interior surface 51 of the anode 50 during use. A preferred material—when the electrolyte is phosphoric acid—is iridium oxide coated titanium.

Figure 2:
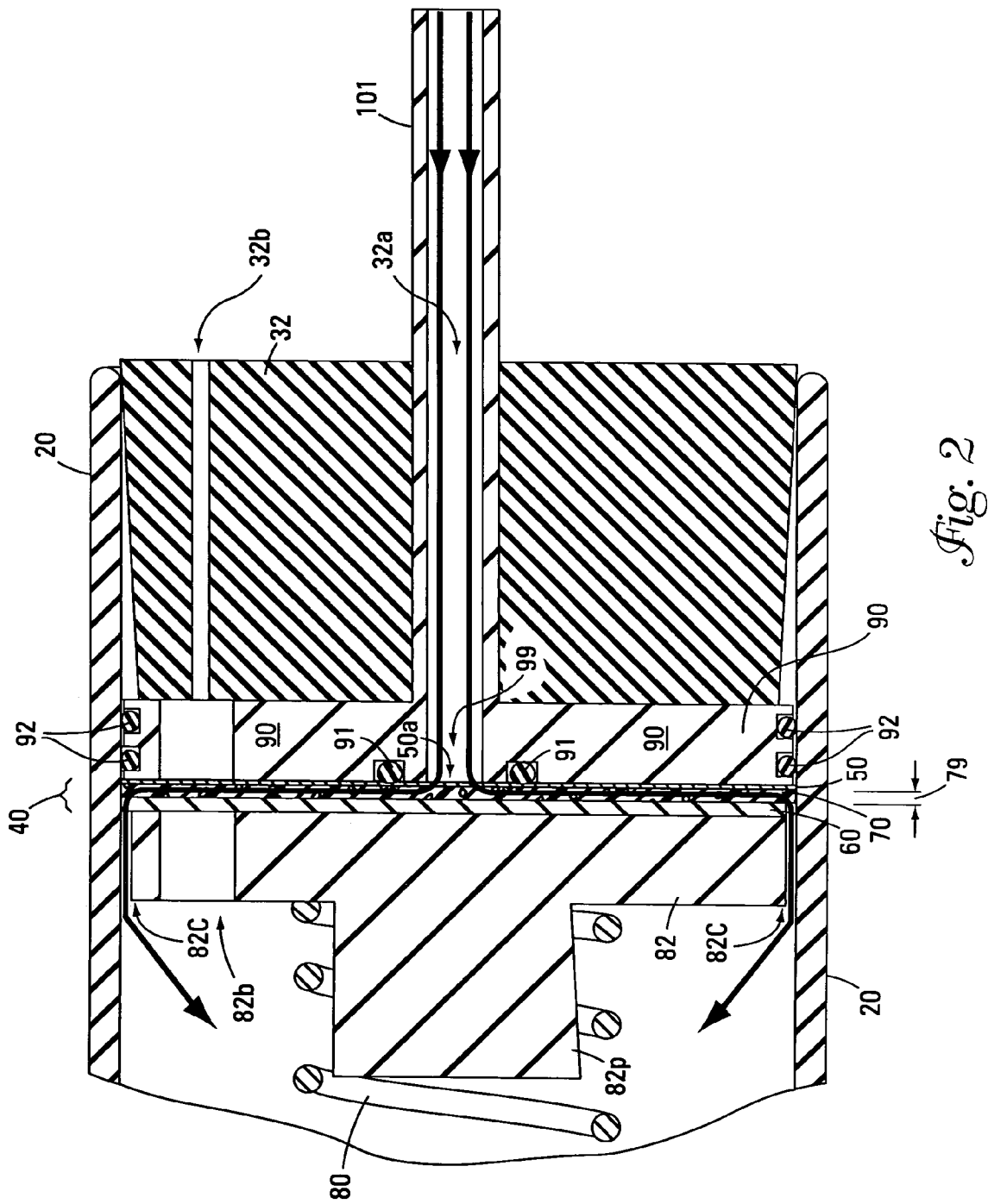
FIG. 2 is an enlarged cross-sectional side view of the inlet end of the invention shown FIG. 1.

As shown in FIGS. 1, 2 and 4, an inlet orifice 50a is provided through a central area (unnumbered) of the anode 50 for permitting passage of a gaseous sample through the anode 50 and into contact with the electrolyte at a central location on the separator 70. Alternatively, when the relative longitudinal positions of the anode 50 and the cathode 60 are switched so that the cathode 60—while remaining connected to a source of negative potential—is positioned upstream from the anode 50—which remains connected to a source of positive potential, this inlet orifice (not shown) would be provided through a central area (unnumbered) of the cathode 60 rather than the anode 50.

Cathode 60

As with the anode 50, the cathode 60 may be constructed from any of the well-known materials suitable for use as a cathode in an electrolytic cell, provided the material can survive extended exposure to the electrolyte and the high concentration of hydrogen evolved at the interior surface 61 of the cathode 60 during use. A preferred material—when the electrolyte is phosphoric acid—is platinum clad niobium.

Electrolyte

The electrolyte may be selected from any of the well-known electrolytes suitable for use in an electrolytic cell. Preferred electrolytes are the liquid electrolytes which are applied as a liquid and then dried. The preferred liquid electrolyte—based predominantly upon its high affinity for the sorption of water vapor in a gaseous sample—for use in the sensor 10 is phosphoric acid applied as a 10% w/w aqueous solution.

The electrolyte is positioned within the gap 79 between the anode 50 and the cathode 60. As a gaseous sample flows through the gap 79, the electrolyte "grabs" any water vapor in the gaseous sample. The "grabbed" water molecules are then promptly ionized into an $O^{-2}$ anion and two $H^+$ cations by the electrical field generated by the anode 50 and the cathode 60 within the gap 79. The $O^{-2}$ anion is attracted to the anode 50 while the $H^+$ cations are attracted to the cathode 60. A detectable electrical signal is generated when the $O^{-2}$ anion is oxidized to O at the anode 50 and the $H^+$ cations are reduced to H at the cathode 60.

Separator 70

As shown in FIGS. 1-4, a separator 70 is provided between the interior-facing major surface 51 of the anode 50 and the interior-facing major surface 61 of the cathode 60. The separator 70 serves as a mechanical separator for creating and maintaining the gap 79 between the anode 50 and the cathode 60, and as a supporting substrate for the electrolyte. Since the separator 70 is in direct physical contact with both the anode 50 and the cathode 60, the separator 70 must be constructed from an electrically insulating material to prevent the generation of false signals. The separator 70 must also be sufficiently porous to permit passage of air and water vapor through the separator with a modest back-pressure. Furthermore, the separator 70 needs to be constructed of a material which (i) is easily wetted by the electrolyte to achieve good conductivity through the insulator to the anode 50 and cathode 60, (ii) doesn't absorb water directly, (iii) can withstand the harsh electrical and chemical environment within the gap 79 (i.e., extended exposure to phosphoric acid, $O^{-2}$, O, $H^+$ and H and the constant presence of an electrical potential) without degradation, and will not contaminate the gaseous sample.

The separator 70 should have a thickness of about 0.2 mm to about 1 mm, preferably 0.2 mm to about 0.8 mm, as an appropriate compromise between a faster response provided with a thinner separator 70 and a longer useful life-span provided by a thicker separator 70 as a result of the increased amount of electrolyte carried by the separator 70.

A variety of materials possessing these necessary and desired characteristics are known to those of skill in the art and commercially available from various sources. Preferred materials are porous ceramics, particularly woven ceramics such as tricot knit zirconium oxide and tricot knot hafnium oxide with modest preference for hafnium oxide due to the presence of yttrium as a stabilizer in zirconium oxide which tend to react with phosphoric acid over time.

In order to ensure contact between the electrolyte and any water vapor in the gaseous sample, the electrolyte is preferably surface coated within the pores (not shown) of the separator 70. This provides a tortuous path of travel for the gaseous sample and a large surface area for retention of electrolyte.

Retention System

As shown in FIGS. 1 and 4, the detection assembly 40 may be conveniently held in place within the lumen 29 of the housing 20 by a retention system (not collectively numbered). The retention system includes (i) a first endcap 31 attached to the housing 20 over the first longitudinal end 21 of the housing 20, (ii) a second endcap 32 attached to the housing 20 over the second longitudinal end 22 of the housing 20, and (iii) a longitudinally aligned sequence of (A) a first support plate 81, (B) a compressed compression spring 80, (C) a second support plate 82, and (D) a sealing plate 90.

Endcaps 31 and 32

As shown in FIG. 1, the endcaps 31 and 32 are attached to the housing 20 over the longitudinal ends 21 and 22 of the housing 20 in such a manner that the endcaps 31 and 32 will remain in a longitudinally fixed position when subjected to an outwardly directed longitudinal force after assembly of the sensor 10. The endcaps 31 and 32 may be secured to the housing 20 by any suitable means including specifically, but not exclusively, adhesive, threaded engagement, friction-fit, welding, pawl and ratchet system, etc. When the housing 20 is constructed from glass, the endcaps 31 and 32 are preferably a high durometer rubber stopper sized for frictional engagement within the ends of the lumen 29.

Spring 80 and Support Plates 81 and 82

As shown in FIG. 1, an outwardly directed longitudinal biasing force is provided by a compressed compression spring 80 concentrically positioned about the longitudinal axis 29x of the lumen 29. The spring 80 is held in position between a first support plate 81 abutting the first endcap 31 and a second support plate 82. The second support plate 82 is configured and arranged so that the plate 82 will longitudinally slide within the lumen 29 and thereby exert the outwardly directed longitudinal biasing force of the spring 80 onto those components positioned between the second support plate 82 and the second endcap 32. If desired, the first support plate 81 may be integrally formed with the first endcap 31.

The spring 80 preferably exerts an outwardly directed force of between about 5 to about 20 psi. A force of less than about 5 psi does not provide sufficient force to ensure dimensional stability of the detection assembly 40 while a force of greater than about 20 psi may crush the separator 70.

The first 81 and second 82 support plates each have a centrally positioned, longitudinally extending post 81p and 82p, respectively, for engaging and retaining the ends (unnumbered) of the spring 80.

The first 81 and second 82 support plates may be constructed from any material possessing sufficient structural integrity, including specifically, but not exclusively, metals such as aluminum, copper, zinc and steel, plastics such as polyethylene, polypropylene, polyvinyl chloride and polyurethane, glass, wood, etc. Metals, such as steel, are generally preferred based upon the high structural integrity, low cost and generally inert nature of most metals.

Sealing Plate 90

As shown in FIG. 1, a sealing plate 90 abuts the second endcap 32 and sandwiches the detection assembly 40 between the second support plate 82 and the sealing plate 90. The sealing plate 90 is positioned upstream from the detection assembly 40 and includes an inlet orifice 90a through the center of the sealing plate 90. An inner O-ring 91 is provided around the inlet orifice 90a for sealing engaging an inlet tube 101. Similarly, an outer O-ring 92 is provided around the periphery of the sealing plate 90 for sealingly engaging the housing 20. If desired, the sealing support plate 90 may be integrally formed with the second endcap 32.

As with the support plates 81 and 82, the sealing plate 90 may be constructed from any material possessing sufficient structural integrity, including specifically, but not exclusively, metals such as aluminum, copper, zinc and steel, plastics such as polyethylene, polypropylene, polyvinyl chloride and polyurethane, glass, wood, etc. Metals, such as stainless steel, are generally preferred based upon the high structural integrity, low cost and generally inert nature of most metals.

Flow Tubes 101 and 102

As shown in FIGS. 1, 2 and 4, an inlet tube 101 is integrally formed with the sealing plate 90 to define inlet orifice 90a through the center of the sealing plate 90, and extends through a longitudinal inlet orifice 32a in the center (unnumbered) of the second endcap 32. An inner O-ring 91 sealing engages the sealing plate 90 and the anode 50 around the inlet orifice 90a through the center of the sealing plate 90. This arrangement permits delivery of a gaseous sample into the gap 79 which is exposed only to the delivery tube 101 and the anode 50 prior to delivery within the gap 79.

The delivery tube 101 may be constructed from any suitably inert material which can form an effective seal with the inner O-ring 91 and will not contaminate a gaseous sample passing through the delivery tube 101. A variety of suitable materials known to those skilled the art may be used, with a preference for stainless steel based upon the highly inert nature of stainless steel.

Figure 3:
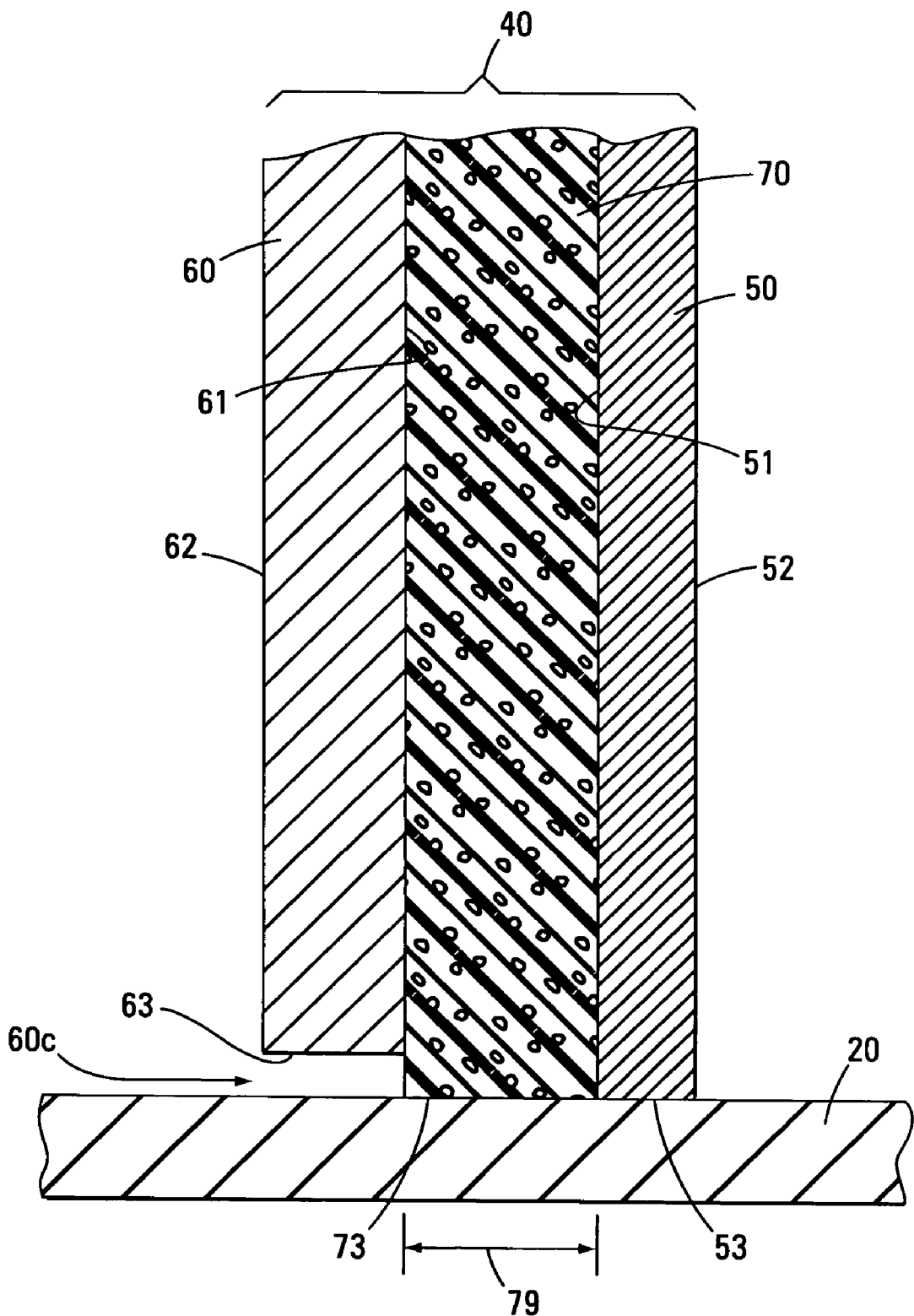
FIG. 3 is a further enlarged cross-sectional side view of a portion of the detection assembly of the invention shown in FIG. 1.

As shown in FIGS. 2 and 3, the periphery of both the cathode 60 and the second support plate 82 is offset from the housing 20 so as to provide a circumferential passageway 60c around the periphery of the cathode 60 and a circumferential passageway 82c around the periphery of the second support plate 82. These circumferential passageways 60c and 82c permit a gaseous sample delivered into the gap 79 to flow radially through the separator 70 and—upon exiting the separator 70 at the outer periphery 73 of the separator 70—to flow through the circumferential passageways 60c and 82c towards the first longitudinal end 21 of the housing 20.

As shown in FIGS. 1, 2 and 3, circumferential passageways 60c and 82c can be conveniently created by employing a cylindrical lumen 29 and a disk-shaped cathode 60 and second support plate 82, and then simply making the diameter of the cathode 60 and the second support plate 82 slightly smaller than the diameter of the lumen 29. When assembled, the undersized cathode 60 and second support plate 82 will only contact the housing 20 at a single point along the periphery of the cathode 60 and second support plate 82, thereby creating a circumferential passageway 60c around the cathode 60 and a circumferential passageway 82c around the second support plate 82.

Alternately, circumferential passageways 60c and 82c can be created by providing at least three radially-extending projections (not shown) uniformly-spaced around the periphery of each of the cathode 60 and the second support plate 82. These projections, such as a raised bump, a longitudinal linear tooth or a cylindrical post, contact the housing 20 and thereby space the periphery of the cathode 60 and the periphery of the second support plate 82 a distance from the housing 20 to create the circumferential passageways 60c and 82c, respectively.

As shown in FIG. 1, an exhaust tube 102 extends through a longitudinal orifice 31a in the center (unnumbered) of the first endcap 31 and through an outlet orifice 81a in the center (unnumbered) of the first support plate 81. The proximal end 102p of the exhaust tube 102 can terminate anywhere from the first endcap 31 to the second support plate 82.

Since the exhaust tube 102 contacts a gaseous sample only after the sample passes through the detection assembly 40, the exhaust tube 102 may be constructed from any material regardless of its ability to form a seal and regardless of whether the material may contaminate the "spent" gaseous sample. While a wide variety of materials may be employed, it is generally most convenient to use the same material for both the inlet tube 101 and the exhaust tube 102.

Electrical Leads

As shown in FIGS. 1 and 2, the anode 50 is connected to the positive half of a source of electricity (not shown) by an anode lead 121 which passes through longitudinally aligned orifices 90b and 32b in the sealing plate 90 in the second endcap 32 respectively. The cathode 60 is connected to the negative half of a source of electricity by a cathode lead 122 which passes through longitudinally aligned orifices 82b, 81b and 31b in the second support plate 82, the first support plate 81 and the first endcap 31 respectively.

A voltage needs to be applied to the anode 50 and cathode 60 to electrolyze any water "grabbed" by the electrolyte. A minimum of about 2 volts is necessary to achieve electrolysis with higher voltages increasing efficiency and responsiveness of the sensor 10 but decreasing the service-life of the sensor 10. Application of about 2 to 20 volts, preferably about 10 to 15 volts, is an effective compromise.

Use

The sensor 10 is used by pumping a gaseous sample through the sensor 10 at a known flow rate. The flow rate should be maintained between a minimum of about 2 $cm^3$/min and a maximum of about 60-120 $cm^3$/min—depending upon the size and porosity of the separator 70. A flow rate of less than about 2 $cm^3$/min is difficult to accurately control while a flow rate of greater than about 60-120 $cm^3$/min can reduce efficiency of the sensor 10 by moving water vapor through the separator 70 with a velocity which limits the ability of the electrolyte to grab and hold onto the water vapor.

A gaseous sample introduced into the inlet tube 101 flows sequentially (i) through the inlet tube 101 past the longitudinal inlet orifice 32a in the center of the second endcap 32 and the longitudinal inlet orifice 90a in the center of the sealing plate 90, (ii) through the inlet orifice 50a in the center of the anode 50, and (iii) into the gap 79 and the pores of the separator 70 where (A) direction of flow changes from an axial flow along the longitudinal axis x of the sensor 10 to a 360° radial flow r from the longitudinal axis x, and (B) the sample is exposed to the electrolyte and the electrical field generated by the anode 50 and the cathode 60.

The spent sample (i.e., the sample after removal of any water-vapor by the detection assembly 40 then exits the sensor 10 by flowing (iv) out from the gap 79 through the outer periphery 73 of the separator 70, (v) through the circumferential passageway 60c in the cathode 60 and the circumferential passageway 82c in the second support plate 82, (vi) past the spring 80, and (vii) into the exhaust tube 102 for travel out of the sensor 10 through the longitudinal outlet orifice 81a in the center of the first support plate 81 and the longitudinal outlet orifice 31a in the center of the first endcap 31.

Upon entry of the gaseous sample into the separator 70, the electrolyte coated onto the surface of the pores in the separator 70 "grab" any water vapor in the gaseous sample. The "grabbed" water molecules are then promptly ionized into an $O^{-2}$ anion and two $H^+$ cations by the electrical field generated by the anode 50 and the cathode 60 within the gap 79. The $O^{-2}$ anion is attracted to the anode 50 while the $H^+$ cations are attracted to the cathode 60. An electrical signal is generated when the $O^{-2}$ anion is oxidized to O at the anode 50 and the $H^+$ cations are reduced to H at the cathode 60. Current generated within the detector 40 is directly proportional to the water disassociated within the detector 40 and follows Faraday's Law. This electrical signal can be detected and measured by standard control systems well known to those of skill in the field.

We claim:

1. A sensor for detecting water vapor in a gaseous sample, comprising (a) an anode, (b) a cathode, (c) an electrolyte intermediate the anode and cathode, (d) an inlet orifice through a central area of the anode or cathode through which the gaseous sample is placed into contact with the electrolyte, and (e) an outlet proximate the periphery of the anode or cathode whereby a gaseous sample introduced through the inlet orifice flows radially through the electrolyte to reach the outlet.

2. The sensor of claim 1 further comprising a porous electrical-insulating separator intermediate the anode and cathode for mechanically separating the anode and cathode while permitting flow of the gaseous sample through the separator.

3. The sensor of claim 2 wherein the electrolyte is surface-coated within the pores of the separator.

4. The sensor of claim 2 wherein the anode is an iridium oxide coated titanium anode.

5. The sensor of claim 2 wherein the cathode is a platinum clad niobium cathode.

6. The sensor of claim 3 wherein the electrolyte is phosphoric acid.

7. The sensor of claim 3 wherein the separator is a woven ceramic oxide separator.

8. The sensor of claim 7 wherein the separator is a woven zirconium oxide separator.

9. The sensor of claim 7 wherein the separator is a woven hafnium oxide separator.

10. The sensor of claim 2 wherein the separator has (i) a first major surface in direct physical contact with an inner surface of the anode, (ii) a second major surface in direct physical contact with an inner surface of the cathode and separated from the first major surface by a thickness of about 0.2 to 1 mm, (iii) a height of about 2 cm to 10 cm, and (iv) a width of about 2 cm to 10 cm.

11. The sensor of claim 10 wherein the separator is a disk having a thickness of about 0.2 to 0.8 mm and a diameter of about 2 to 6 cm.

12. A water vapor sensor, comprising (a) an anode having an interior-facing major surface and an exterior-facing major surface, (b) a cathode having an interior-facing major surface and an exterior-facing major surface, (c) a porous electrical-insulating separator between the interior-facing major surfaces of the anode and the cathode defining a gap between the interior-facing major surfaces of the anode and the cathode, and (d) an electrolyte within the gap, (e) an inlet orifice through the anode or cathode through which a gaseous sample is introduced into a central area of the gap, and (f) an outlet circumscribing the gap through which a gaseous sample introduced into the gap through the inlet orifice exits the gap, whereby a gaseous sample introduced through the inlet orifice flows radially through the electrolyte to reach the outlet.

13. The sensor of claim 12 wherein the electrolyte is surface-coated within the pores of the separator.

14. The sensor of claim 12 wherein the anode is an iridium oxide coated titanium anode.

15. The sensor of claim 12 wherein the cathode is a platinum clad niobium cathode.

16. The sensor of claim 13 wherein the electrolyte is phosphoric acid.

17. The sensor of claim 13 wherein the separator is a woven ceramic oxide separator.

18. The sensor of claim 17 wherein the separator is a woven zirconium oxide separator.

19. The sensor of claim 17 wherein the separator is a woven hafnium oxide separator.

20. The sensor of claim 12 wherein the separator has (i) a first major surface in direct physical contact with an inner surface of the anode, (ii) a second major surface in direct physical contact with an inner surface of the cathode and separated from the first major surface by a thickness of about 0.2 to 1 mm, (iii) a height of about 2 cm to 10 cm, and (iv) a width of about 2 cm to 10 cm.

21. The sensor of claim 20 wherein the separator is a disk having a thickness of about 0.2 to 0.8 mm and a diameter of about 2 to 6 cm.

* * * * *